United States Patent [19]
Pirela-Cruz

[11] Patent Number: 5,136,743
[45] Date of Patent: Aug. 11, 1992

[54] DISTAL RADIOULNAR JOINT STRESS PLATFORM

[75] Inventor: Miquel Pirela-Cruz, Albuquerque, N. Mex.

[73] Assignee: The United States of America as represented by the Secretary of the Air Force, Washington, D.C.

[21] Appl. No.: 734,010

[22] Filed: Jul. 22, 1991

[51] Int. Cl.$^5$ .............................................. A61G 13/12
[52] U.S. Cl. ...................................... 5/647; 128/878; 378/208
[58] Field of Search ............................ 5/623, 647, 646; 128/878, 879, 877, 21; 378/208, 180

[56] References Cited

U.S. PATENT DOCUMENTS

| | | | |
|---|---|---|---|
| 3,715,587 | 2/1973 | Burkhalter et al. | 378/180 |
| 4,232,681 | 11/1980 | Tulaszewski | 128/653 |
| 4,265,232 | 5/1981 | Stonich | 128/133 |
| 4,674,110 | 6/1987 | Eaton et al. | 378/208 |
| 4,798,199 | 1/1989 | Hubbard et al. | 128/87 R |
| 4,827,496 | 5/1989 | Cheney | 378/180 |

OTHER PUBLICATIONS

"Stress Computed Tomography Analysis of the Distal Radioulnar Joint: A Diagnostic Tool for Determining Translational Motion", by Pirela-Cruz et al, J. Hand Surg 16A: 1,75-82 (Jan. 1991).

*Primary Examiner*—Alexander Grosz
*Attorney, Agent, or Firm*—Bobby D. Scearce; Donald J. Singer

[57] ABSTRACT

A device for positioning the distal radioulnar joint (DRUJ) for medical examination is described which comprises a platform sized to receive a forearm and hand of a subject, a pair of upright blocks mounted on the platform in spaced relationship to each other, each block having a plurality of slots therethrough, a post on the platform near one end thereof for gripping by the subject in substantially immobilizing the forearm against lengthwise movement along the platform during examination, and a pair of stabilizing posts adjustably mounted to each block for contacting corresponding sides of the forearm near the DRUJ and holding the forearm in preselected position for examination of the DRUJ.

5 Claims, 1 Drawing Sheet

DISTAL RADIOULNAR JOINT STRESS PLATFORM

RIGHTS OF THE GOVERNMENT

The invention described herein may be manufactured and used by or for the Government of the United States for all governmental purposes without the payment of any royalty.

BACKGROUND OF THE INVENTION

The invention relates generally to devices for positioning the upper extremity during a computerized axial tomography (CAT) scan, and more particularly to a device for accurately positioning of the distal radioulnar joint for examination.

The prior art is deficient in consistent objective criteria and methods for evaluating subluxation in the distal radioulnar joint (DRUJ). Typical methods for evaluating subluxation or translation motion in the DRUJ includes computerized axial tomography (CAT) analysis and x-ray radiography. The CAT scan is a preferable method for the evaluation of the DRUJ by providing a coronal cross-sectional image of the radius and ulna. Moreover, radiographs can be misleading because a slight rotational change (10°) in position of the joint may appear as a subluxation, instability or dislocation in the joint and therefore may not allow satisfactory visualization of the joint.

The invention solves or substantially reduces in importance shortcomings in prior radiographic examinations by providing a platform for positioning and retaining the forearm of a subject for CAT scan of the DRUJ. The device comprises a base on which two blocks are mounted and support a plurality of adjustable positioning posts for holding the radius in position and applying a selected degree of stress on the ulna. The invention allows stress to be applied to the radius and ulna to assess stability in the DRUJ.

It is therefore a principal object of the invention to provide a device for positioning the arm for CAT scan.

It is another object of the invention to provide a device for positioning the distal radioulnar joint for CAT scan or x-ray.

These and other objects of the invention will become apparent as a detailed description of representative embodiments proceeds.

SUMMARY OF THE INVENTION

In accordance with the foregoing principles and objects of the invention, a device for positioning the distal radioulnar joint for medical examination is described which comprises a platform sized to receive a forearm and hand of a subject, a pair of upright blocks mounted on the platform in spaced relationship to each other, each block having a plurality of slots therethrough, a post on the platform near one end thereof for gripping by the subject in substantially immobilizing the forearm against lengthwise movement along the platform during examination, and a pair of stabilizing posts adjustably mounted to each block for contacting corresponding sides of the forearm near the distal radioulnar joint and holding the forearm in preselected position for examination of the distal radioulnar joint.

DESCRIPTION OF THE DRAWINGS

The invention will be more clearly understood from the following detailed description of representative embodiments thereof read in conjunction with the accompanying drawings wherein.

DETAILED DESCRIPTION

Evaluations of distal radioulnar joints in a group of volunteer subjects using a special stress computed tomography technique which utilized in part the positioning and stabilizing device described herein is described in Pirela-Cruz et al, "Stress Computed Tomography Analysis of the Distal Radioulnar Joint: A Diagnostic Tool for Determining Translational Motion", The Journal of Hand Surgery 16A.1, 75–82 (Jan 1991), the entire teachings of which are incorporated herein by reference.

Figure 1:
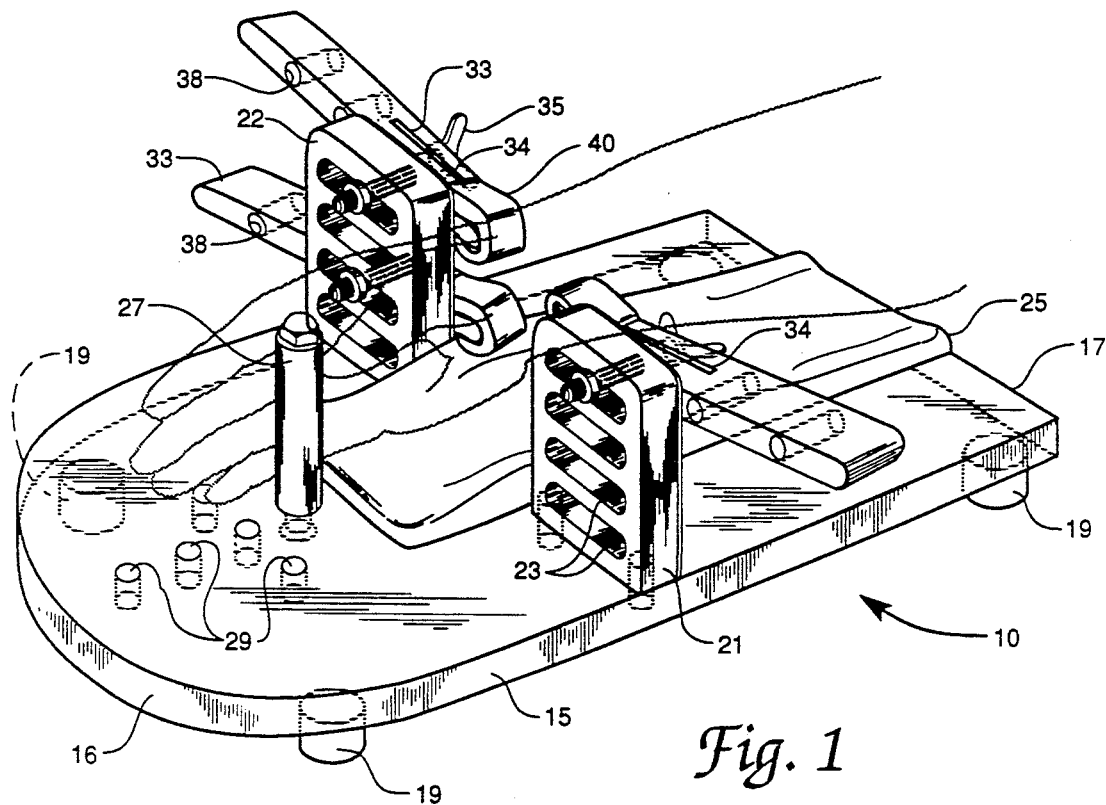
FIG. 1 shows a first perspective view of the restraining and positioning device structured according to the invention.
Figure 2:
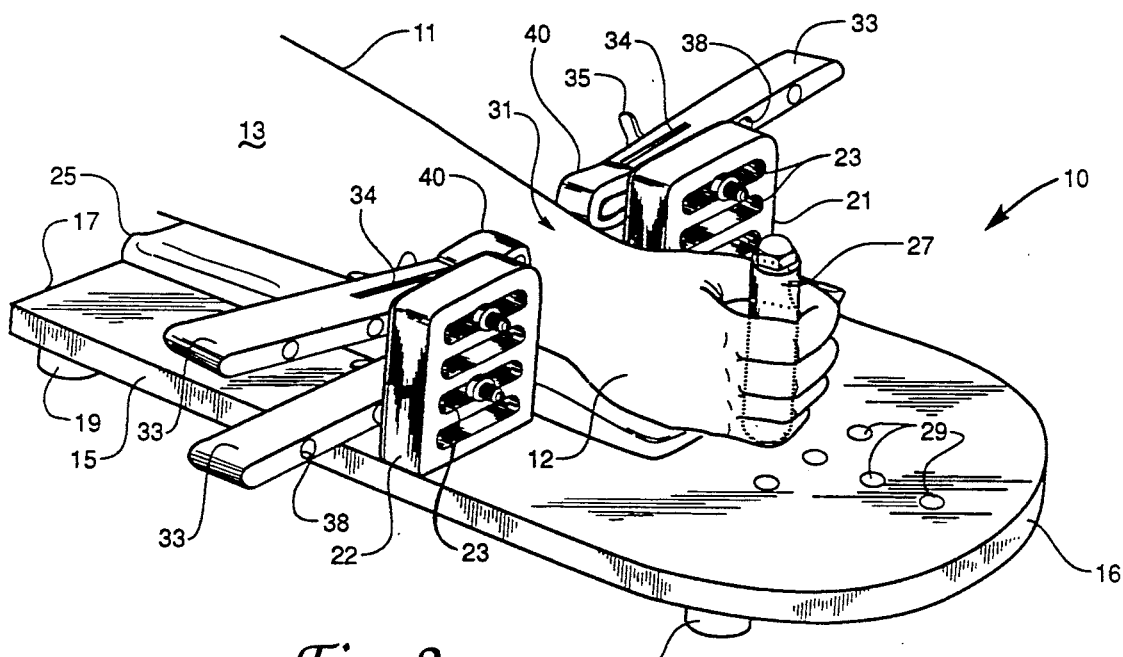
FIG. 2 shows a second perspective view of the FIG. 1 device with the arm of a subject positioned therein.

Referring now to the drawings, FIG. 1 shows a perspective view of a restraining and positioning device 10 structured according to the invention. FIG. 2 shows device 10 with forearm 11 and hand 12 of subject 13 positioned thereon. Device 10 includes platform 15 having a first (forward) end 16 and a second (rearward) end 17 and being sized to comfortably receive forearm 11 and hand 12. Platform 15 may be supported by a plurality of optional legs 19. A pair of blocks 21,22 each with a plurality of slots 23 therein are disposed on platform 15 in spaced relationship to each other as suggested in FIGS. 1,2. Pad 25 of any suitable material is disposed along a lengthwise portion of platform 15 between blocks 21,22 to support and cushion forearm 11 in position for CAT scan, x-ray or other procedure. Post 27 is located near forward end 16 of platform 15 for gripping by subject 13, the gripping action serving in part to substantially immobilize forearm 11 against lengthwise movement along platform 15 during examination. Post 27 may be configured to be selectively insertable into any of a plurality of positioning holes 29 in platform 15 to accommodate a forearm of substantially any length, or to selectively stress radioulnar joint 31 in the assessment of stability in the joint.

One or a pair of stabilizing posts 33 are adjustably mounted to blocks 21,22 using positioning screws 35 inserted through selected holes 38 in posts 33 and along selected slots 23 in blocks 21,22 according to the size of forearm 11. Each stabilizing post 33 includes a flared cushioned end portion 40 for contacting and firmly and comfortably holding forearm 11 at joint 31 in position for examination, and further includes along the length thereof a groove or marker 34 to aid in reproducibly positioning forearm 11 within device 10. The purpose of the two superior posts is to firmly hold the radius in position, and the purpose of the two posts on the inferior aspect is to stress the ulna, such as in the volar and dorsal planes.

The various elements of device 10 may be constructed of any suitable material, as would occur to the skilled artisan, preferably of a material transparent to radiation used in any of the medical examination procedures for which use device 10 may be contemplated, and may include plastic, Plexiglas TM, or the like.

In a device 10 fabricated as a demonstration unit, platform 15, legs 19, post 27, blocks 21,22 and stabilizing posts 33 were fabricated of Plexiglas TM to be transparent to penetrating radiation; screws 35 were fabricated of titanium in order to reduce background scatter of x-rays during examination, although it is noted that screws of material transparent to penetrating radiation may be desirable. Pad 17 was Styrofoam TM. In the demonstration unit, platform 15 measured 43×20 cm, blocks 21,22 were 5×9.5 cm, posts 33 were about 17 cm long and post 27 was 9.5 cm high located nominally about 11 cm from blocks 21,22.

A General Electric 9800 scanner was used in at least sixteen CAT scans of DRUJs in eight subjects in demonstration of the utility of the invention. Satisfactory CAT scans of the DRUJ in male and female subjects with a range of forearm sizes were performed with neutral forearm rotation in each of three positions providing neutral, maximal ulnar volar stress, and maximal ulnar dorsal stress. The DRUJ was stressed by stabilizing the radius and having the subject grip post 33 to stress the ulna.

The invention therefore provides a device for accurately positioning the distal radioulnar joint for CAT scanning, x-ray or other clinical procedure. It is understood that modifications to the invention may be made as might occur to one skilled in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

I claim:

1. A device for positioning and stabilizing the arm of a subject for CAT scanning, radiography or other clinical examination, comprising:

(a) a platform having a first end and a second end, said platform being sized to receive a forearm and hand of said subject;

(b) a pair of upright blocks mounted on said platform in spaced relationship to each other, each of said blocks having a plurality of slots therethrough;

(c) a post disposed on said platform near said first end thereof for gripping by said subject in substantially immobilizing said forearm against lengthwise movement along said platform during examination; and (d) a pair of stabilizing posts adjustably mounted to each of said blocks for contacting corresponding sides of said forearm near the distal radioulnar joint and holding said forearm in preselected position for examination of said distal radioulnar joint.

2. The device of claim 1 further comprising a pad on said platform disposed along a lengthwise portion of said platform between said upright blocks for cushioning said arm of said subject during examination.

3. The device of claim 1 further comprising a plurality of holes defined in said platform near said first end thereof for receiving said post in selectively positioning said post on said platform, in accommodating forearms of various lengths and in selectively stressing said distal radioulnar joint.

4. The device of claim 1 further comprising flared cushioned end portions on each of said stabilizing posts for contacting and firmly and comfortably holding said forearm at said distal radioulnar joint.

5. The device of claim 1 wherein said platform, blocks, post and stabilizing posts comprise a material which is substantially transparent material to radiation.

* * * * *